United States Patent
Alsobayel et al.

(10) Patent No.: US 12,426,804 B1
(45) Date of Patent: Sep. 30, 2025

(54) SYSTEM AND METHOD FOR ALLEVIATING LOWER BACK PAIN

(71) Applicant: KING SAUD UNIVERSITY, Riyadh (SA)

(72) Inventors: Hana Ibrahim Alsobayel, Riyadh (SA); Hend Suliman Alkhalifa, Riyadh (SA); Kholoud Abdullah Almufaireej, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/061,955

(22) Filed: Feb. 24, 2025

(51) Int. Cl.
| A61B 5/11 | (2006.01) |
| A61B 5/00 | (2006.01) |
| A61B 5/0205 | (2006.01) |
| G01P 15/14 | (2013.01) |
| G16H 20/30 | (2018.01) |

(52) U.S. Cl.
CPC ............ *A61B 5/11* (2013.01); *A61B 5/02055* (2013.01); *A61B 5/6823* (2013.01); *A61B 5/742* (2013.01); *G01P 15/14* (2013.01); *G16H 20/30* (2018.01); *A61B 2562/0219* (2013.01)

(58) Field of Classification Search
CPC ..... A61B 5/11; A61B 5/02055; A61B 5/6823; A61B 5/742; A61B 2562/0219; G01P 15/14; G16H 20/30
See application file for complete search history.

(56) References Cited

U.S. PATENT DOCUMENTS

| 7,457,439 | B1 * | 11/2008 | Madsen | G06T 7/251 |
| | | | | 348/154 |
| 9,782,122 | B1 * | 10/2017 | Pulliam | A61B 5/4839 |
| 10,335,080 | B2 * | 7/2019 | Vaidyanathan | A61B 5/1123 |
| 10,406,434 | B1 * | 9/2019 | Uehara | A63F 13/212 |
| 12,014,824 | B1 * | 6/2024 | Mirza | G16H 40/67 |
| 12,029,942 | B2 * | 7/2024 | McInturf | A63B 71/0622 |

(Continued)

FOREIGN PATENT DOCUMENTS

CN 114974507 A 8/2022

OTHER PUBLICATIONS

ZI Hao Guo, et al., "A Wearable Multidimensional Motion Sensor for AI-Enhanced VR Sports", DOI: 10.34133/research.0154, Published May 25, 2023.

(Continued)

*Primary Examiner* — Laura Martin
*Assistant Examiner* — Philip L Cotey
(74) *Attorney, Agent, or Firm* — Nath, Goldberg & Meyer; Joshua B. Goldberg (57) ABSTRACT

A system and method for improving lower back pain including using a virtual reality (VR) or an augmented reality (AR) headset for performing exercises aimed at reducing lower back pain. A gyroscopic sensor can be placed on the user's lower back to collect movement data of the lower back while the user engages with the headset. The headset may include a headpiece that can be fastened to the user's head with an elastic band and a mobile phone selectively connectable to the headpiece. The screen of the mobile phone is directed toward the user such that the user can see it. The screen can be used to display interactive exercises that the user can perform to alleviate lower back pain. The difficulty level of the exercises can be varied based on user performance.

17 Claims, 8 Drawing Sheets

(56) References Cited

U.S. PATENT DOCUMENTS

| | | | | |
|---|---|---|---|---|
| 2010/0211135 A1* | 8/2010 | Caparso | ............... | G16H 20/70 607/62 |
| 2015/0025335 A1* | 1/2015 | Jain | ............... | A61B 5/1102 600/509 |
| 2015/0065919 A1* | 3/2015 | Cuevas | ............... | A61B 5/746 600/587 |
| 2016/0005320 A1* | 1/2016 | deCharms | ............... | G09B 19/00 434/236 |
| 2018/0256939 A1* | 9/2018 | Malcolm | ............... | A63B 24/0062 |
| 2018/0264318 A1* | 9/2018 | Fung | ............... | A63F 13/65 |
| 2018/0330810 A1* | 11/2018 | Gamarnik | ............... | G16H 10/20 |
| 2019/0269970 A1* | 9/2019 | Canavan | ............... | A63B 24/0062 |
| 2019/0290209 A1* | 9/2019 | Fu | ............... | A61B 5/7264 |
| 2020/0015713 A1* | 1/2020 | Chang | ............... | G01P 15/00 |
| 2020/0025713 A1* | 1/2020 | Liu | ............... | G01N 33/5438 |
| 2020/0038708 A1* | 2/2020 | Cheu | ............... | A63B 71/0622 |
| 2020/0085366 A1* | 3/2020 | Benson | ............... | A61B 5/4566 |
| 2021/0298642 A1* | 9/2021 | Pena | ............... | A61B 5/4824 |
| 2022/0249019 A1* | 8/2022 | Wang | ............... | A61B 5/1118 |
| 2022/0262504 A1* | 8/2022 | Bratty | ............... | G16H 20/30 |
| 2024/0122535 A1* | 4/2024 | Rees | ............... | A61B 5/742 |
| 2024/0324902 A1* | 10/2024 | Matijevich | ............... | A61B 5/6801 |
| 2025/0195877 A1* | 6/2025 | Schulte | ............... | G16H 50/20 |

OTHER PUBLICATIONS

Ferdews Tlili, et al., "Design and architecture of smart belt for real-time posture monitoring" DOI: 10.1016/j.iot.2021, Published Oct. 22, 2021.

Prof. Bharati Pandhare, et al., "Smart waist belt using internet of things", ISSN: 2320-2882, Published Mar. 3, 2021.

Qi Wang, et al., "A Smart Garment for Posture Monitoring", DOI: https://doi.org/10.1145/2851581.2890262, Published May 7, 2016.

Xinxin Huang, et al., "Sensor-Based Wearable Systems for Monitoring Human Motion and Posture", DOI: 10.3390/s23229047, Published Nov. 8, 2023.

* cited by examiner

SYSTEM AND METHOD FOR ALLEVIATING LOWER BACK PAIN

TECHNICAL FIELD

The present disclosure relates to a system and method for alleviating lower back pain through exercise.

DISCUSSION OF THE RELATED ART

Lower back pain is a common problem affecting individuals worldwide. Traditional methods of managing lower back pain, such as physical therapy, medication and exercise, while effective, may be costly and often require a significant amount of time and effort to be put in by an individual to potentially alleviate the pain. The time, cost and/or effort required by these methods can often discourage persons with lower back pain from taking steps to improve their health condition.

SUMMARY

The present disclosure relates to a system and method for exercising to alleviate lower back pain. The system and method of the present subject matter is designed to encourage persons suffering from lower back pain to perform exercises intended to alleviate lower back pain.

The present subject matter includes using an application software (App), running on a mobile device (e.g., a smartphone), programmed to engage a user in performing physical exercises aimed at reducing lower back pain.

A user of the App can wear a vest made of a flexible fabric material. A gyroscopic sensor can be removably attached to the back side of the vest, in an area corresponding to the lower back of the wearer, to track the motion of the wearer's lower back. The motion data obtained from the gyroscopic sensor can be received by the user's mobile device, and can be input to the App. The processor of the mobile device running the App can be used to interpret the received data to determine whether the user performed a particular type of exercise (e.g., flexion of the lower back, etc.,) and whether the user performed it correctly (e.g., whether the user bent the lower back to a predetermined degree). The App can be used to award the user with points for each correctly performed exercise. This course of action incentivizes the user to perform the exercises indicated by the App and to do so correctly, which in turn, can help alleviate the user's lower back pain.

The process of awarding the user points can also be used to incentivize the user to increase the number of exercises performed (by continuing to engage with the App) and, based on the circumstances, to incentivize the user to increase the level of difficulty of the exercises, within reason, to help reduce the user's lower back pain.

For example, when a user can bend the lower back forward by a small amount, the App can encourage the user to perform the same exercise again, when a predetermined number of conditions are met, to bend the lower back forward slightly more.

The App can be embodied as a game where the user is encouraged to follow along in performing the game steps, which result in actions that can reduce lower back pain.

The mobile device running the App can be used as a virtual reality device or as an augmented reality device. This can be accomplished by selectively attaching the mobile device to a headset worn by a user with the screen of the mobile device facing the user (or being placed in front of the user's eyes).

In this configuration, since the screen of the mobile phone is all that a user sees while engaging with the system and method of the present subject matter, the instant disclosure can provide an immersive experience, designed to encourage users in performing fun tasks, the completion of which can reduce lower back pain.

Additional sensors can be selectively connected to the user's body to gather real-time data of the user's vitals. This information can be used to adjust the difficulty level of the game up or down (e.g., to make the exercises easier or more difficult, to increase the speed of performing the exercises, to reduce the speed of performing the exercises, etc.,) to optimize the beneficial impact of the present system and method on a user while keeping the user interested in performing exercises aimed at reducing lower back pain.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

The order of the method steps described in this specification does not limit the present subject matter thereto. The method steps described in this specification may be performed in the order presented in the specification, or in a different order, unless the context clearly indicates otherwise.

Referring to FIG. 1, a method for alleviating lower back pain includes selectively affixing a first gyroscopic sensor to the lower back region of a user (Step S101). The affixing step may include, for example, providing the user with a vest made of a flexible fabric material (to allow flexibility of movement) with the vest having a pouch, a pocket, hook and loop fasteners, etc., arranged at the lower back region of the vest. According to this configuration, when the user wears the vest, the first gyroscopic sensor can be placed in the pouch, pocket, etc. such that it is "selectively affixed" to the lower back region of the user. For the avoidance of doubt, "selectively affixed" can but does not necessarily require direct contact of the first gyroscopic sensor with the skin of the user, but merely requires the first gyroscopic sensor to be immobilized in a relatively static position relative to the lower back of the user such that the first gyroscopic sensor can receive, e.g., angular motion data of the user's back, as well as other desired data.

Figure 1A:
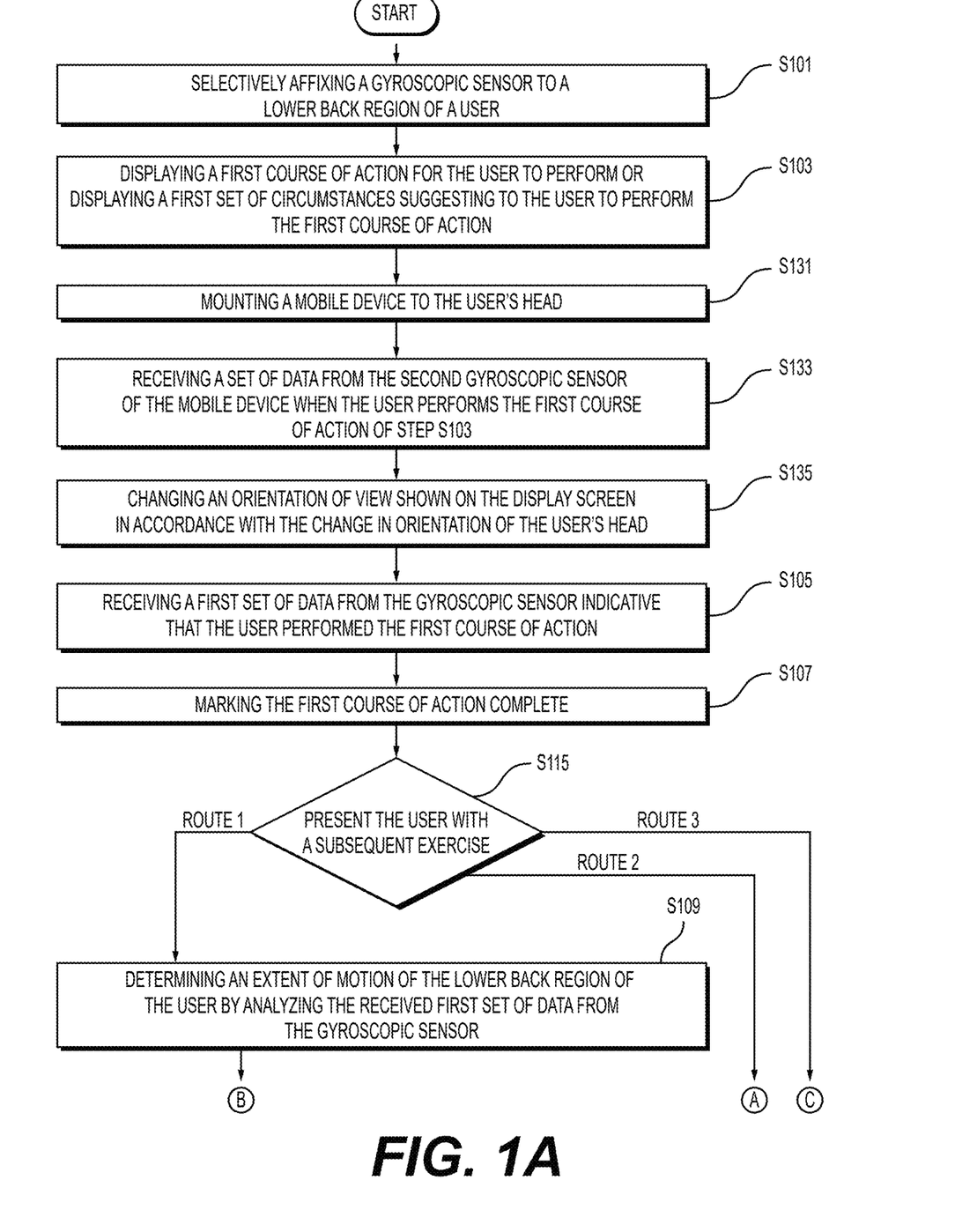
FIGS. 1A-1D are flowcharts illustrating a method for alleviating lower back pain in accordance with an embodiment of the present disclosure.

In this regard, the pouch, pocket, hook and loop fastener, etc., can be used to selectively and securely affix a gyroscopic sensor to the lower back region of the user when the user wears the vest. This way, the gyroscopic sensor can be used to obtain angular motion data of the user's lower back, including roll, pitch and yaw, resulting from the user's movements.

Alternatively, step S101 may include affixing an inertial motion unit (IMU) to the lower back region of a user, the IMU being a device that includes an accelerometer and a gyrometer. This specification will refer to the motion tracking device placed on the user's lower back as a gyroscopic sensor or a first gyroscopic sensor for convenience of explanation but with the understanding that said device can be either a gyroscopic sensor or an IMU.

The gyroscopic sensor can be centered on the user's back, directly behind the spine. Step S101 may include disposing the gyroscopic sensor at a position (or height) of the user's back that ranges from the location of the user's lumbar spine to about the junction between the lumbar spine and the thoracic spine. The gyroscopic sensor may even be placed slightly above the border between the lumbar spine and the thoracic spine.

While the vest provides one way of securing the gyroscopic sensor to the user's back, the gyroscopic sensor can also be selectively affixed to the location of the user's back via different means, for example, via an adhesive material directly adhering the gyroscopic sensor to the user's skin on the lower back, by using an article of fabric sufficiently tightened to keep the gyroscopic sensor securely connected to the user's lower back, etc.

Step S103 includes displaying on a display screen, visible to the user, a first course of action for the user to perform or displaying on the display screen a first set of circumstances that can be interpreted as suggesting to the user to perform the first course of action.

Step S103 may include using an application software (App) programmed to engage the user in performing physical exercises designed to work the lower back region in a way that can alleviate lower back pain. The App can run on a mobile device, for example, on a smartphone, a tablet, etc. A display screen of the mobile device can be used to show the user exercises for the user to perform.

A headpiece configured to be worn on the user's head can be used to selectively and securely hold the mobile device in front of the user's eyes with the display screen of the mobile device oriented toward the user's eyes. For example, the headpiece may include a headband and a holding structure configured to be selectively connected to the mobile device. The headband can be used to secure the headpiece to the user's head and the mobile device and be selectively connected to the holding structure.

This configuration provides an immersive virtual reality (VR) or augmented reality (AR) experience of interacting with the App. This, in turn, encourages users to interact with the system and method of the present disclosure, thereby improving the users' physical health condition and alleviating their lower back pain by exercising.

The App may be embodied, for example, as a game where the user is tasked with performing certain physical activities that require moving the lower back in various directions that may cause the user's spine (including the lower portion of the spine) to undergo flexion, extension, rotation and lateral flexion.

Merely as a non-limiting example, the game may include a character running forward, flying forward, or otherwise moving in the forward direction. Then, obstacles may appear in the path of movement of the game character. In order to keep the user engaged with the game, for example, to keep the game character in good health and continuing to move forward, the user may wish to move the user's body in a way that would prevent the game character from colliding with the obstacle in the path ahead since the user has a first-person view of the game character through the screen of the mobile device placed in front of the users eyes.

The movement of the user's body, caused by the user's desire to prevent the game character from colliding with the obstacle shown in the screen, may cause the lower portion of the user's spine to undergo flexion, extension, rotation or lateral flexion, depending on the type of evasive maneuver performed by the user.

Figure 2:
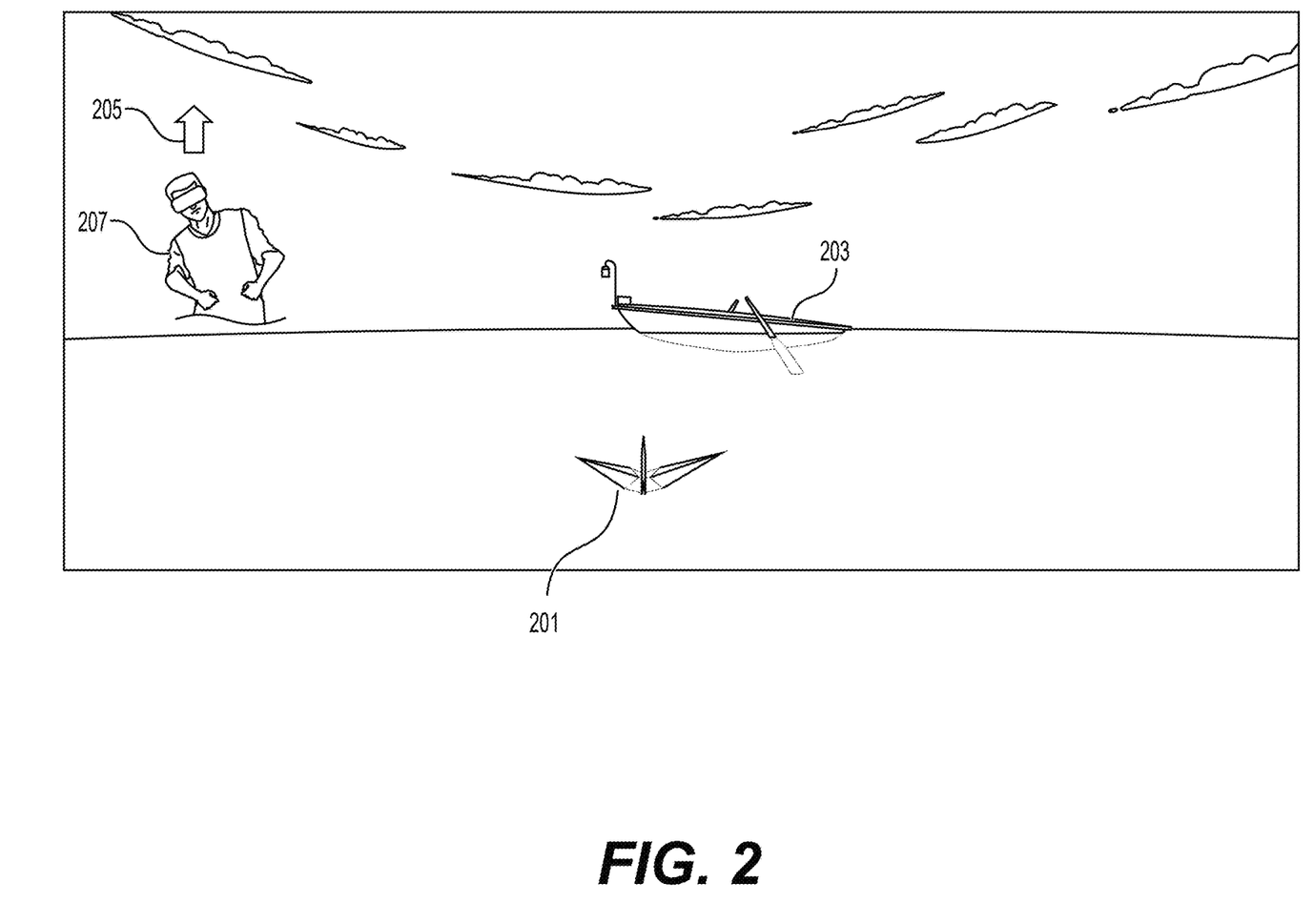
FIG. 2 is a screenshot of an application software (App) programmed to engage a user in performing physical exercises for alleviating lower back pain in accordance with the method of FIG. 1.

FIG. 2 illustrates an exemplary App game screen as taken during game play. The headpiece that the user wears may block ambient light from all directions. Therefore, the screen of the mobile device is all that a user may see while engaging with the system and method of the present subject matter. This configuration increases the user's concentration in playing the game, thereby reducing lower back pain by performing exercises that cause the lower back of the user to be moved in different directions.

In the exemplary screen shot of FIG. 2, the user may control the movement of a game character 201 that resembles a bird. As illustrated in FIG. 2, the character 201 is moving (or flying) forward, but an obstacle in the form of a boat 203 is placed in the moving path of the character 201.

The obstacle 203 placed in the path of movement of the game character 201 is one example of a set of circumstances that may be the "first set of circumstances that can be interpreted as suggesting to the user to perform the first course of action" in step S203. The first course of action would be, for example, a movement of the user's body, including the user's spinal cord, that would serve as an evasive maneuver on the part of the game character 201.

For example, when the user sees that the game character 201 is approaching the boat 203, the user may tilt, rotate, turn, or otherwise move the user's head and body in a direction away from the boat 203. This movement is akin to the way that a person would normally move to avoid collision with a real (as opposed to virtual) oncoming object. The movement of the user's body that was performed to avoid a collision between the game character 201 and the boat 203 would steer the game character 201 away from colliding with the obstacle 203. For example, the movement of the user's head would be detected by a gyroscope of the mobile device running the App, and the gyroscopic data from the gyroscope of the mobile device would be used to turn the game character 201 in the same way as that which the user's head was turned (or bent). That is, the game character would mimic the movement of the user's head.

For example, with reference to FIG. 2, the set of circumstances illustrated in FIG. 2 may suggest to the user to perform an extension exercise (a backward bending of the spine with the head turning to look up) such that the character 201 would change the flight path from flying horizontally to flying at an incline (or flying upwardly) to gain elevation and fly over the boat 203. Alternatively, the set of circumstances illustrated in FIG. 2 may suggest to the user to rotate the user's head and torso left or right (causing rotation of the spine in the left or right direction) such that the character 201 would veer to the left or to the right to avoid colliding with the boat 203, etc.

The "displaying a first course of action for the user to perform," referred to in step S203 may include, for example, displaying a graphical indication on the screen suggesting a course of action for the user to take. As exemplarily illustrated in FIG. 2, a directional arrow 205 at the top left region of the game screen can be displayed to indicate to the user a course of action for the user to take. The directional arrow 205 points upwardly, indicating that the user should bend the spine backwardly with the head turning to look up such that the game character 203 can fly upwardly over the boat 203 to avoid colliding with the boat 203.

The use of the arrow 205 is merely exemplary to illustrate the concept of the present subject matter. Other graphical symbols, sounds, etc., can be used to indicate to a user a suggested course of action. For example, a graphical interpretation of a person bending the torso and the head to the left hand side, as illustrated by the graphical symbol 207 in FIG. 2, may be used to indicate to the user to bend the torso to the left hand side to exercise the user's lower back, and to bend the user's head to the left hand side such that the character 201 can veer to the left to avoid colliding with the boat 203.

The App may be designed such that movements of the game character would require the user to move the user's head and back by a degree that is reasonable, without being overly strenuous, while effectively alleviating the user's lower back pain.

Referring to FIG. 1, the method includes receiving a first set of data from the gyroscopic sensor placed on the user's back, the first set of data being indicative that the user performed the first course of action (Step S105).

For example, when the user bends the user's spine backwardly and raises the user's head upwardly to cause the game character 201 to fly over the boat 203, the gyroscopic sensor placed on the user's back detects the bending of the spine backwardly (extension of the spine).

Upon receiving the first set of data from the gyroscopic sensor, the method of FIG. 1 may include marking the first course of action complete (Step S107). Step S107 may also include awarding point(s) to the user in the game, displaying on the display screen visual confirmation that the user performed the first course of action, emitting a sound indicative of a successful completion of a task, etc., to reward the user for interacting with the App. The reward may incentivize the user to continue engaging with the App and, in turn, continuing to perform exercises aimed at reducing lower back pain.

Referring to FIG. 1, the method may include determining an extent of motion of the lower back region of the user by analyzing the received first set of data from the gyroscopic sensor (Step S109) and comparing the determined extent of motion with a predetermined threshold motion value (Step S111).

Figure 1B:
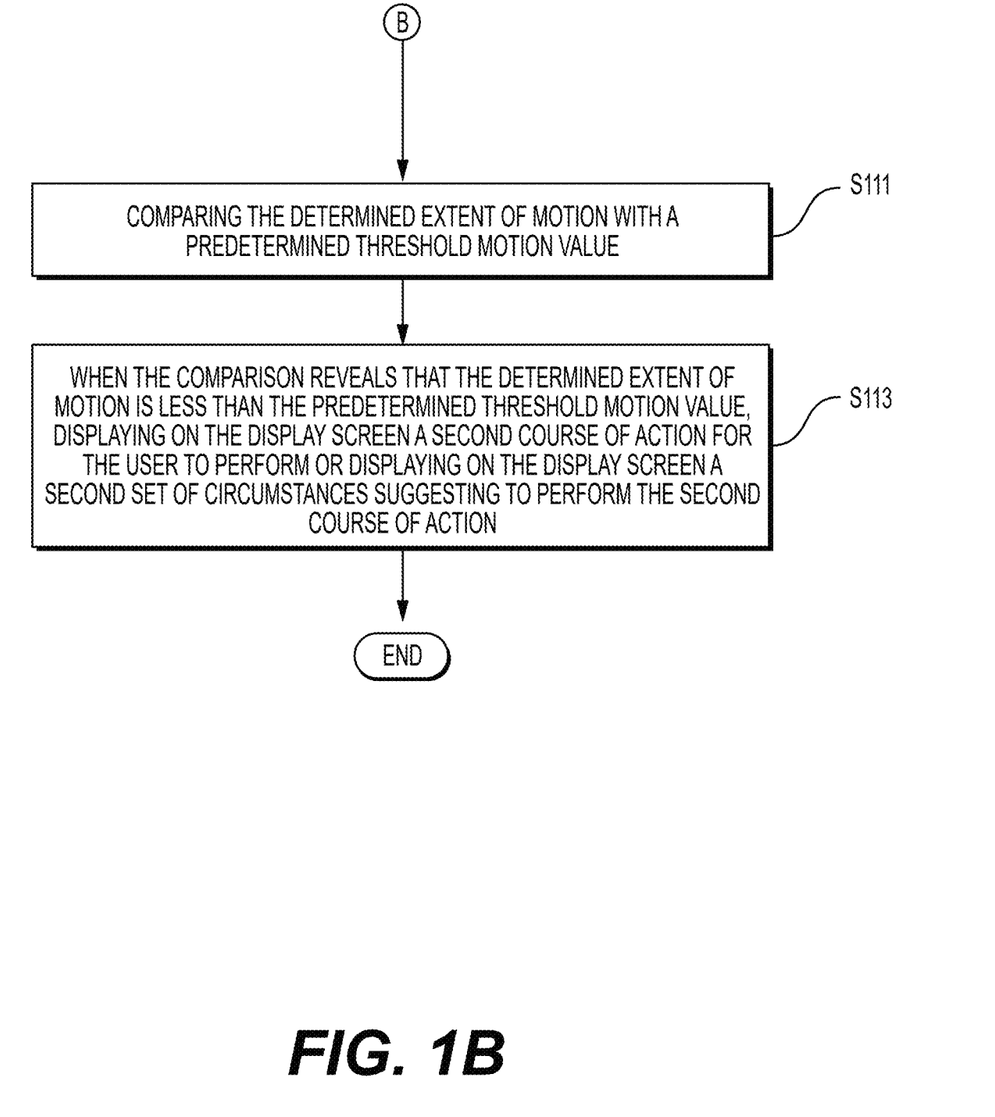

When the comparison reveals that the determined extent of motion of the user's back is less than the predetermined threshold motion value, the method may include displaying on the display screen a second course of action for the user to perform or displaying on the display screen a second set of circumstances that can be interpreted as suggesting to the user to perform the second course of action (Step S113).

For example, when the comparison step S109 reveals that the user did not move the user's back by a sufficient degree when performing the evasive maneuver in avoiding collision with the boat 203 (that is, when the comparison step reveals that the determined extent of motion of the user's back is less than the predetermined threshold motion value), the App may be configured to present the user with a second course of action for the user to perform (e.g., to repeat the same evasive maneuver performed previously or to perform a different movement that exercises the lower back) or displaying on the display screen a second set of circumstances that can be interpreted as suggesting to the user to perform the second course of action (e.g., placing another obstacle on the path of movement of the game character 201 for the user to avoid by taking an evasive maneuver).

The second course of action may be similar to the first course of action, the same as the first course, or different from the first course of action. In other words, the second exercise (or second evasive maneuver) can be the same as the first exercise, similar to the first exercise, or different from the first exercise.

Step S113 may also include displaying on the screen visual indica to encourage the user to increase the user's extent of motion when performing the second course of action. For example, step S113 may include presenting the user with text and/or symbols on the screen encouraging the user to move by a greater degree when seeking to avoid the next obstacle, by emitting sounds and/or audible instructions encouraging the user to move by a greater degree when seeking to avoid the next obstacle, etc.

Steps S109-S113 can encourage the user to increase the user's limited range of motion of the lower back, thereby improving the user's health and increasing the efficacy of the interactive exercises in alleviating the user's back pain.

Subsequent to step S113, the method may include repeating the algorithm described with reference to steps S105-S113 but for the course of action that was performed last. For example, and after the performance of Step S113 regarding the second set of circumstances and the second course of action, the method may include marking the second course of action as complete, similarly to step S107 (which marks the first course of action complete), determining an extent of motion of the lower back region of the user for the second course of action by analyzing the received second set of data from the gyroscopic sensor (similarly to step S109, which determines the extent of motion for the first set of data), comparing the determined extent of motion for the second course of action with a predetermined motion threshold motion value, similarly to step S111, and when the comparison reveals that the determined extent of motion is less than the predetermined threshold motion value, displaying on the display screen a third course of action for the user to perform or displaying on the display screen a third set of circumstances suggesting to the user to perform the third course of action, similar to step S113. This process can be continued for as many courses of action as is desired, i.e., the steps herein can include third, fourth, fifth, etc. courses of action for the user to perform.

Alternatively, the method of FIG. 1 may be used to present the user with a subsequent exercise (Step S115) to perform after having performed the first course of action of step S103 without comparing the extent of the user's range of motion as described with reference to steps S109-S113.

Figure 1C:
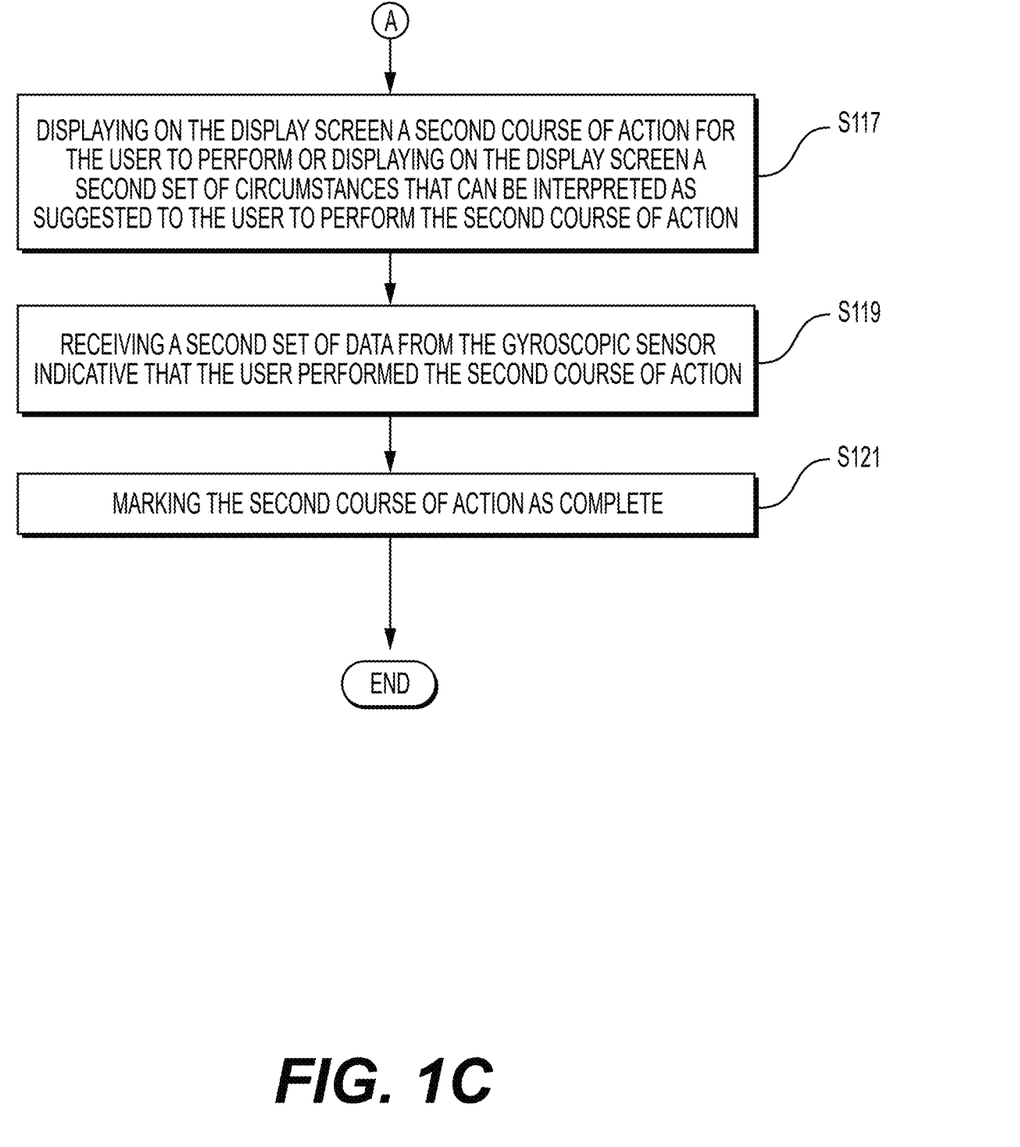

For example, after the completion of step S107, the method may include displaying on the display screen a second course of action for the user to perform or displaying on the display screen a second set of circumstances that can be interpreted as suggesting to the user to perform the second course of action (Step S117), receiving a second set of data from the gyroscopic sensor indicative that the user performed the second course of action (Step S119), and marking the second course of action as complete (step S121). The second course of action may the different from the first course of action of step S103, the same as the first course of action of step S103, or similar to the first course of action of step S103.

In another approach, after having performed step S107, the method may include considering input from sensors attached to the user's body that provide vital data (e.g., heart beat rate), to determine whether to change the level of difficulty of the exercises that will be presented to the user while engaging with the App (e.g., to continue evading obstacles placed on the movement path of the character 201).

For example, in step S123, the method may include attaching to the user's body at least one vital sensor selected from the group consisting of a heart beat rate monitoring sensor, a blood oxygen level monitoring sensor, a blood pressure level monitoring sensor and a temperature sensor.

Step S125 may include receiving vitals data from the at least one vital sensor when the user performs the first course of action (after the performance of step S103).

Step S127 may include determining to increase a level of difficulty for a second course of action for the user to perform based on the received vitals data, relative to a level of difficulty of the first course of action.

More broadly, step S127 includes considering whether to increase the difficulty of the game, decrease the difficulty of game, or maintain the same level of difficulty of the game for the subsequent exercise that the user will perform.

In step S127, the determination to increase, decrease or keep the level of difficulty the same can be made by considering the received vitals data. When the vitals data indicates that the vitals of the user are below a predetermined threshold, the level of difficulty of the game can be increased for the subsequent exercise. For example, when the temperature of the user is below a predefined threshold temperature, when the heart beat rate of the user is below a predefined threshold heart beat rate level, and so on, the level of difficulty of the game may be raised.

The increase in level of difficulty may include, for example, presenting the user on the screen with more objects to avoid collision with per unit time, presenting the user with exercises (e.g., evasive maneuvers) that require the user's back to bend by a greater degree, etc., In step S127, when the vitals are within a predetermined threshold range, the level of difficulty of the game can be kept unchanged. On the other hand, when the vitals exceed a predetermined threshold range (e.g., the user's blood pressure level, heat beat rate, etc., exceeds a predetermined threshold level), the level of difficulty of the game can be reduced.

Step S129 includes displaying on the display screen the second course of action for the user to perform (the level of difficulty of the second course of action being raised, lowered or kept the same as the level of difficulty of the first course of action as described in step S127), or displaying on the display screen a second set of circumstances that can be interpreted as suggesting to the user to perform the second course of action.

A combination of the steps described with reference to the group of steps S109-113, the group of steps S117-S121, and the group of steps S123-S129 can be made when desiring to incorporate the feature of comparing the extent of motion of the user's back with a predetermined motion threshold value and/or the feature of potentially change the difficulty level of the game for the next exercise that will be presented to the user.

In an approach, the method of FIG. 1 may include selectively mounting the mobile device to the user's head (Step S131) with the display screen of the mobile device being visible to the user as described in this specification. Step S131 can be performed prior to receiving the first set of data of step S105. The mobile device may include a second gyroscopic sensor in its housing (e.g., the gyroscopic sensor of the mobile device).

Figure 1D:
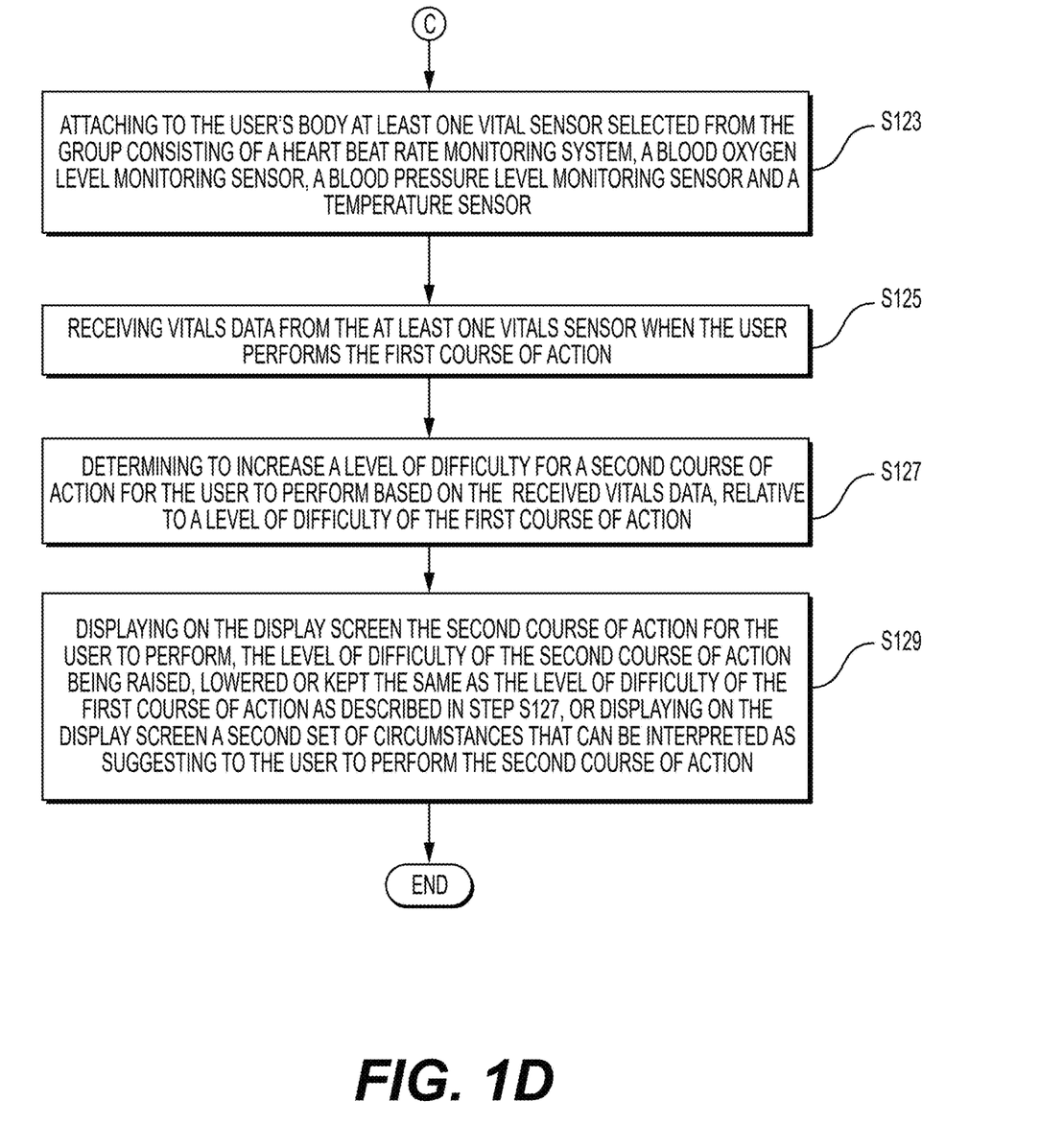

In this approach, the method may include step S133, receiving a set of data from the second gyroscopic sensor of the mobile device when the user performs the first course of action of step S103, the received set of data from the second gyroscopic sensor indicating that the user changed an orientation of the user's head (e.g., due to taking the evasive action to avoid collision with the boat 203).

The method may then include changing an orientation a view shown on the display screen in accordance with the change in orientation of the user's head (Step S135). Referencing the example above when the user bends the spine backwardly with the head turning upwardly such that the character 201 can fly over the obstacle 203, step S135 may include changing the orientation of the view shown on the display screen by tilting the first-person view of the game (as shown to the user via the mobile device screen) upwardly, to match the user's motion of rotating the head upwardly. The process of orienting the view on the screen based on the head movements of the user provides an interactive and pleasant user experience that reduces lower back pain.

Steps S117-S121, S125-S129 and/or S133-S135 can be performed repetitively to keep the user engaged with the App until a certain action occurs, for example, until the user quits the App, until the character 201 "runs out of life" by colliding into a barrier, etc., as the case may be.

The App embodying a program with a character that should avoid obstacles in the path ahead is merely exemplarily and is not intended to limit the scope of the present subject matter thereto. The App may be programmed differently to engage the user in performing exercises for the lower back. For example, the App may be programmed to engage the user in picking up an exercise ball in virtual or augmented reality on the screen of the mobile device fastened to the user's head (with the user picking up a ball in real life if desired for a realistic experience) and to instruct the user to, for example, bend to the left and drop the ball off, bend to the right and drop the ball off, etc., to exercise the user's lower back.

Figures 3, 4:
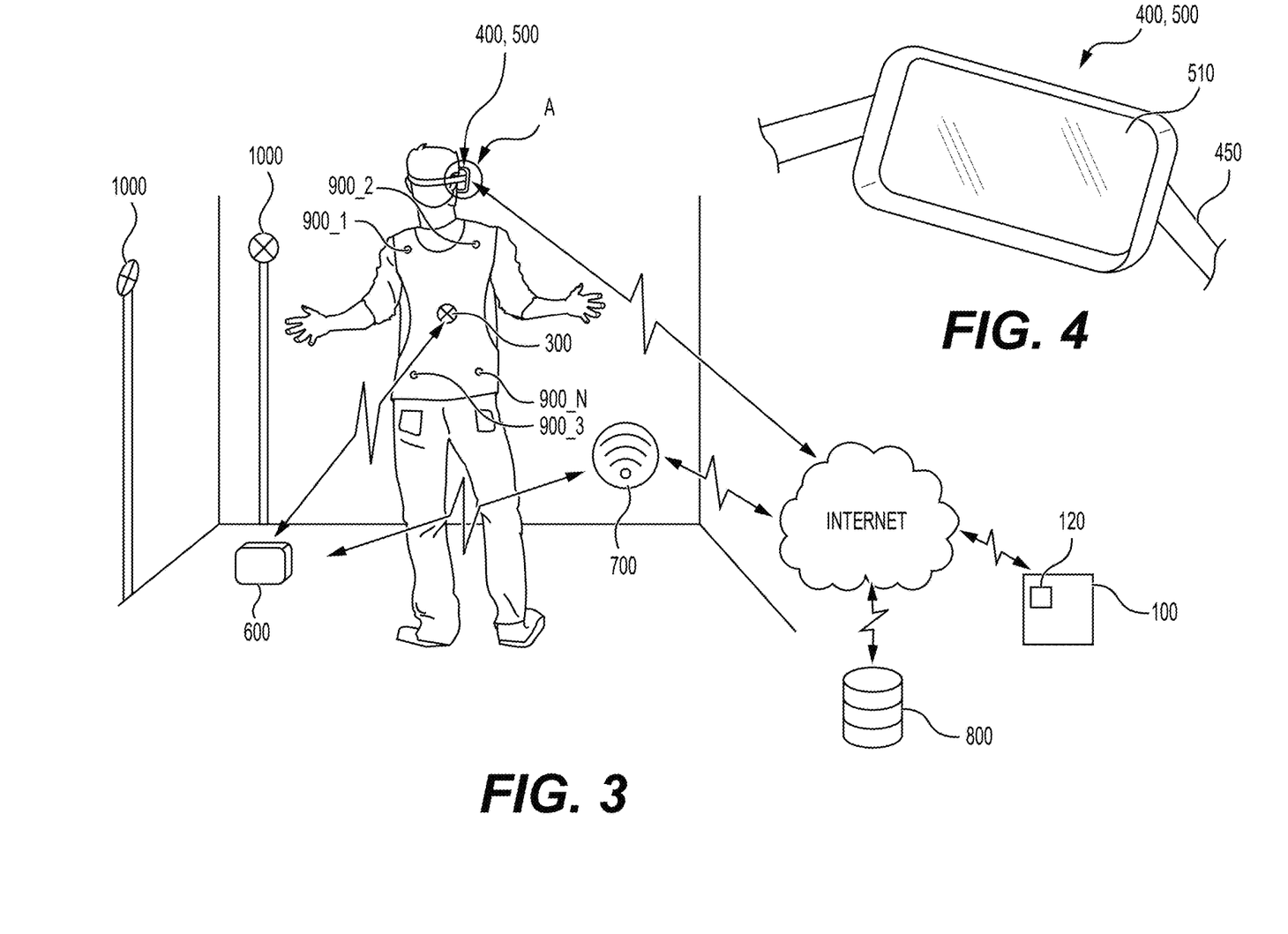
FIG. 3 is a diagram illustrating a system for alleviating lower back pain in accordance with an embodiment of the present disclosure.
FIG. 4 is a magnified perspective view illustrating a region A of FIG. 3.

Referring to FIG. 3, a system for alleviating lower back pain may include a computer 100 having a processor 120, a wearable article 200 made of fabric material (e.g., a vest, as described in this specification), a first gyroscopic sensor 300, a headpiece 400 configured to be worn on a user's head, a mobile device 500 configured to be selectively connected to the headpiece 400, a second computer 600 (e.g., a low power computing device running the Arduino open source code or the like) a router 700, a database 800, and a plurality of vital sensors 900-1 to 900_N, with "N" being a positive nonzero integer.

While the system of FIG. 3 may include the plurality of vital sensors 900_1 to 900_N, the system of FIG. 3 may alternative include one vital sensor selected from the group consisting of the vital sensors 900_1 to 900_N, or more than one vital sensor selected from the group consisting of the vital sensors 900_1 to 900_N.

The computer 100, the first gyroscopic sensor 300, the mobile device 500, the second computer 600, the database 800 and the vital sensors 900_1 to 900_N may be communicatively coupled to one another via the router 700 and the Internet, or directly.

The computer 100 may be, for example, a personal computer, a server, etc. The processor 120 of the computer 100 may be configured to perform the steps of a method for alleviating lower back pain, as described in this specification. That is, the processor 100 does not need to be physically located with, e.g., the gyroscopic sensor and the present apparatus, methods, and systems can be performed by remotely connecting to the processor 100.

A user profile may be stored for each user of the system of FIG. 3 in the database 800. In addition, the achievements of each user, for example, a tally of the points accumulated by using the system of FIG. 3 for performing the method steps described in this specification can be stored in the database 800.

Referring to FIG. 3-6, the headpiece 400 is configured to be worn on the user's head. The headpiece 400 may include a holding structure 410 configured to be selectively connected to the mobile device 500 via a receiving space 420 in the holding structure 410, and an elastic band 450 configured to be fastened around a user's head.

The mobile device 500 may have a display screen 510 disposed on a first side surface thereof (see FIG. 5), a camera 520 disposed on a second side surface thereof (see FIG. 6), and a second gyroscopic sensor 530. The first and second side surfaces of the mobile device 500 may be opposite to one another.

Figure 5:
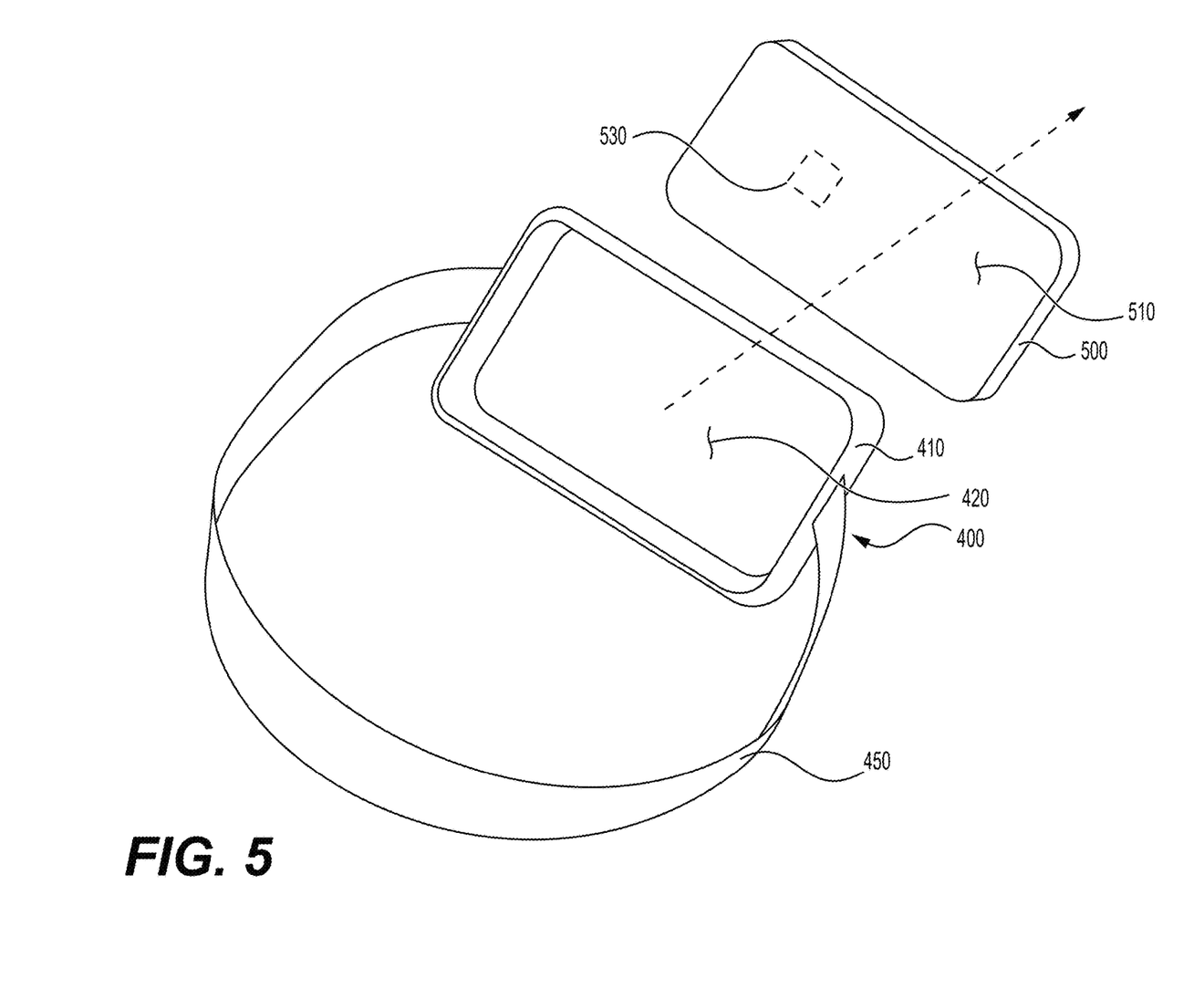
FIG. 5 is an exploded perspective view illustrating a headpiece and a mobile device depicted in region A of FIG. 3.
Figure 6:
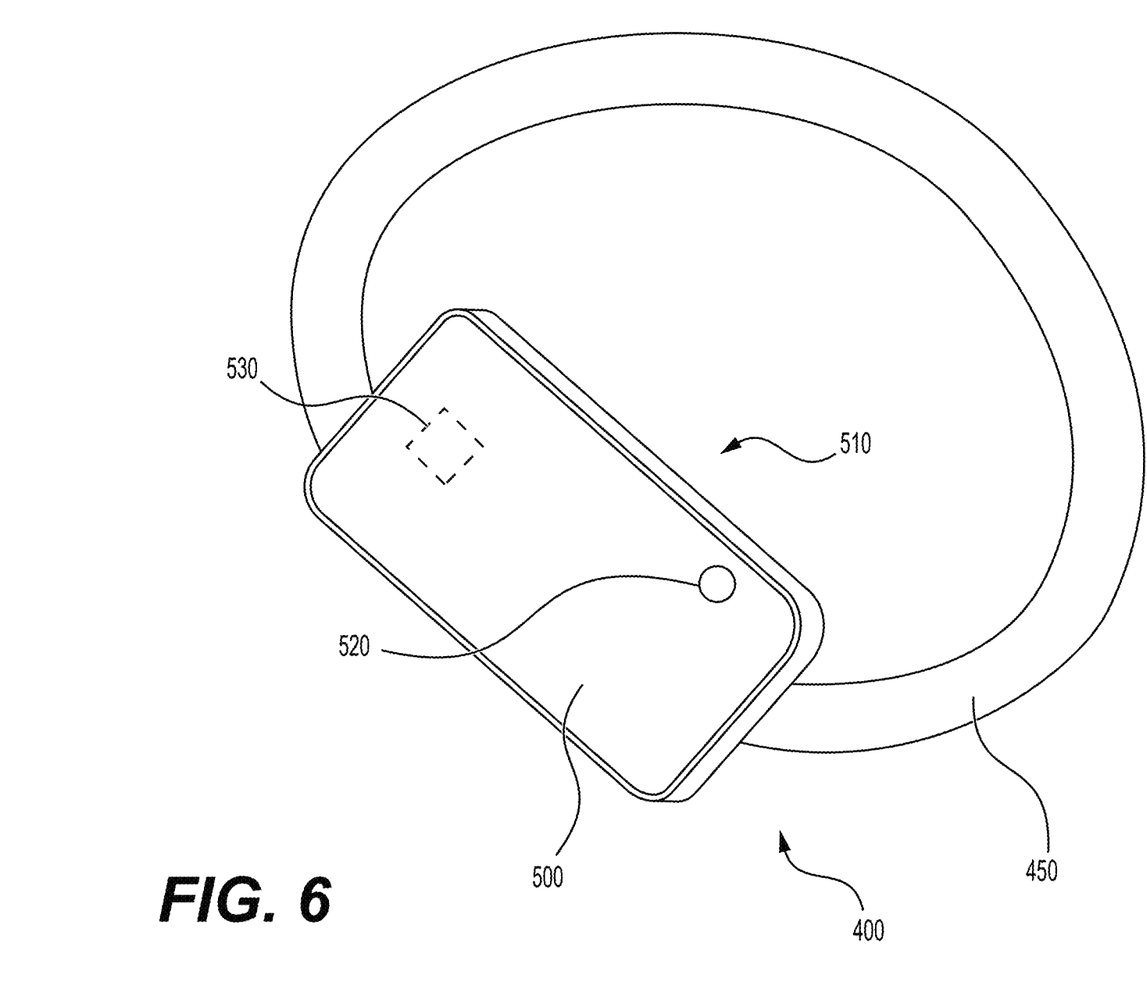
FIG. 6 is a perspective view illustrating the headpiece and mobile device of FIG. 3.

The mobile device 500 may be coupled to the holding structure 410 of the headpiece 400 in a way that orients the display screen 510 to face the user's eyes (or to be visible to the user) with the camera 520 pointing away from the user.

The second computer 600 may be communicatively coupled to the first gyroscopic sensor 300, to the mobile device 500 and to the vital sensors 900_1 to 900_N wirelessly or by wire. The computer 100 may receive data from the first gyroscopic sensor 300, data from the vital sensors 900_1 to 900_N, data from the second gyroscopic sensor 530 and data from the camera 520 of the mobile device 500 in real-time. For example, the second computer 600 may transmit data received from the first gyroscopic sensor 300, data received from the vital sensors 900_1 to 900_N and data received from the second gyroscopic sensor 530 and the camera 520 of the mobile device 500 to the computer 100 for processing.

The computer 100 may include a non-transitory, tangible program storage medium, embodying a program of instructions executable by the processor to perform method steps for alleviating lower back pain as described in this specification.

A method of using the system of FIG. 3 may include selectively affixing the first gyroscopic sensor 300 to a lower back region of a user (e.g., by having the user wear a vest as described in this specification with the first gyroscopic sensor 300 connected to the vest), connecting one or more of the vital sensors 900-1 to 900_N to the user (which may be placed in direct contact with the user's body), placing the headpiece 400 on the user's head, and selectively connecting the mobile device 500 to the holding structure with the display screen 510 of the mobile device being visible to the user.

Then, the method steps as described in this specification with reference to FIG. 1 can be carried out to exercise the user and to reduce the user's lower back pain.

While the processor 120 of the computer 100 is described as the processor being used to perform the steps of a method for alleviating lower back pain, as described in this specification, a processor included in the second computer 600 or a processor included in the mobile device 500 may also be used for performing the method steps of this specification if said processor(s) have sufficient capacity to do so.

Referring to FIG. 1, markers 1000, such as symbols, signs, or other visual indicia, can be placed at different locations of the room where the user is located. Since the mobile device 500 mounted to the user's head includes the camera 520 facing away (or pointing away) from the user's eyes (when the screen 510 of the mobile device faces the user's eyes), the markers 1000, as captured by the camera 520, can be used to calibrate the mobile device 500.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. A method for alleviating lower back pain in a user, the method comprising:
   selectively affixing a first gyroscopic sensor to a lower back region of the user;
   attaching to the user's body at least one vital sensor selected from the group consisting of a heart beat rate monitoring sensor, a blood oxygen level monitoring sensor, a blood pressure level monitoring sensor and a temperature sensor;
   displaying on a display screen, visible to the user, a first course of action for the user to perform or displaying on the display screen a first set of circumstances that can be interpreted as suggesting to the user to perform the first course of action, the first course of action being a physical exercise intended to be performed by the user to exercise the user's lower back region;
   receiving vitals data from the at least one vital sensor when the user performs the first course of action;
   receiving a first set of data from the first gyroscopic sensor indicative that the user performed the first course of action;
   marking the first course of action as complete based on the received first set of data from the first gyroscopic sensor;
   determining an extent of motion of the lower back region of the user by analyzing the received first set of data from the first gyroscopic sensor;
   determining to increase, decrease, or maintain a level of difficulty for a second course of action for the user to perform based on:
      a) the received vitals data, relative to a level of difficulty of the first course of action, and
      b) an extent of motion of the lower back region of the user, determined by analyzing the received first set of data from the first gyroscopic sensor, and comparing said analysis of the first set of data with a predetermined threshold motion value,
   the second course of action being a physical exercise intended to be performed by the user to exercise the user's lower back region; and
   displaying on the display screen the second course of action for the user to perform or displaying on the display screen a second set of circumstances that can be interpreted as suggesting to the user to perform the second course of action, the level of difficulty of the second course of action being increased, decreased or maintained relative to the level of difficulty of the first course of action based on the determining step.

2. The method of claim 1, wherein the second course of action has a same level of difficulty as the first course of action.

3. The method of claim 1, wherein the second course of action has a higher level of difficulty than the first course of action.

4. The method of claim 1, further comprising:
   receiving a second set of data from the first gyroscopic sensor indicative that the user performed the second course of action; and
   marking the second course of action as complete based on the received second set of data.

5. The method of claim 1, wherein the display screen is a component of a mobile device, said mobile device including a second gyroscopic sensor therein;
   the method further comprising:
   mounting the mobile device to the user's head;
   receiving a set of data from the second gyroscopic sensor when the user performs the first course of action, the received set of data from the second gyroscopic sensor indicating that the user changed an orientation of the user's head; and
   changing an orientation a view shown on the display screen in accordance with the change in orientation of the user's head.

6. The method of claim 1, wherein the second course of action has a lower level of difficulty than the first course of action.

7. A system for alleviating lower back pain, comprising:
   a processor;
   a set of devices including a first gyroscopic sensor, a display screen, and at least one vital sensor selected from the group consisting of a heart beat rate monitoring sensor, a blood oxygen level monitoring sensor, a blood pressure level monitoring sensor and a temperature sensor; and
   a non-transitory, tangible program storage medium, readable by the system for alleviating lower back pain, embodying a program of instructions executable by the processor to perform method steps for alleviating lower back pain, the method steps comprising:
   providing instructions for selectively affixing the first gyroscopic sensor to a lower back region of a user;
   providing instructions for attaching to the user's body the at least one vital sensor selected from the group consisting of a heart beat rate monitoring sensor, a blood oxygen level monitoring sensor, a blood pressure level monitoring sensor and a temperature sensor;
   displaying on the display screen, visible to the user, a first course of action for the user to perform or displaying on the display screen a first set of circumstances that can be interpreted as suggesting to the user to perform the first course of action, the first course of action being a physical exercise intended to be performed by the user to exercise the user's lower back region;
   receiving vitals data from the at least one vital sensor when the user performs the first course of action;
   receiving a first set of data from the first gyroscopic sensor indicative that the user performed the first course of action;

marking the first course of action as complete based on the received first set of data from the first gyroscopic sensor;
determining an extent of motion of the lower back region of the user by analyzing the received first set of data from the first gyroscopic sensor;
determining to increase, decrease, or maintain a level of difficulty for a second course of action for the user to perform based on:
  a) the received vitals data, relative to a level of difficulty of the first course of action, and
  b) an extent of motion of the lower back region of the user, determined by analyzing the received first set of data from the first gyroscopic sensor, and comparing said analysis of the first set of data with a predetermined threshold motion value,
  the second course of action being a physical exercise intended to be performed by the user to exercise the user's lower back region; and
displaying on the display screen the second course of action for the user to perform or displaying on the display screen a second set of circumstances that can be interpreted as suggesting to the user to perform the second course of action, the level of difficulty of the second course of action being increased, decreased or maintained relative to the level of difficulty of the first course of action based on the determining step.

8. The system of claim 7, wherein the set of devices further comprises:
a mobile device, said mobile device including the display screen and a second gyroscopic sensor; and
a headpiece configured to be worn on the user's head, the headpiece including a holding structure configured to be selectively connected to the mobile device;
wherein the method steps further comprise:
providing instructions for placing the headpiece on the user's head;
providing instructions for selectively connecting the mobile device to the holding structure with the display screen of the mobile device being visible to the user;
receiving a set of data from the second gyroscopic sensor when the user performs the first course of action, the received set of data from the second gyroscopic sensor indicating that the user changed an orientation of the user's head; and
changing an orientation a view shown on the display screen in accordance with the change of the orientation of the user's head.

9. The system of claim 8, wherein the mobile device is communicatively coupled to the first gyroscopic sensor by wire.

10. The system of claim 8, wherein the mobile device is communicatively coupled to the first gyroscopic sensor wirelessly.

11. The system of claim 8, wherein the mobile device is communicatively coupled to the first gyroscopic sensor via the Internet.

12. The system of claim 2, wherein the second course of action has a same level of difficulty as the first course of action.

13. The system of claim 7, wherein the second course of action has a higher level of difficulty than the first course of action.

14. The system of claim 7, wherein the method steps further comprise:

receiving a second set of data from the first gyroscopic sensor indicative that the user performed the second course of action; and
marking the second course of action as complete based on the received second set of data.

15. The system of claim 7, wherein the second course of action has a lower level of difficulty than the first course of action.

16. A system for alleviating lower back pain, comprising:
a processor;
a set of devices including a first gyroscopic sensor; a mobile device, said mobile device including a display screen and a second gyroscopic sensor; a headpiece configured to be worn on the user's head, the headpiece including a holding structure configured to be selectively connected to the mobile device; and at least one vital sensor selected from the group consisting of a heart beat rate monitoring sensor, a blood oxygen level monitoring sensor, a blood pressure level monitoring sensor and a temperature sensor; and
a non-transitory, tangible program storage medium, readable by the system for alleviating lower back pain, embodying a program of instructions executable by the processor to perform method steps for alleviating lower back pain, the method steps comprising:
providing instructions for selectively affixing the first gyroscopic sensor to a lower back region of a user;
providing instructions for placing the headpiece on the user's head;
providing instructions for selectively connecting the mobile device to the holding structure with the display screen of the mobile device being visible to the user;
providing instructions for attaching to the user's body the at least one vital sensor selected from the group consisting of the heart beat rate monitoring sensor, the blood oxygen level monitoring sensor, the blood pressure level monitoring sensor and the temperature sensor;
displaying on the display screen a first course of action for the user to perform or displaying on the display screen a first set of circumstances that can be interpreted as suggesting to the user to perform the first course of action;
receiving a first set of data from the first gyroscopic sensor indicative that the user performed the first course of action;
receiving a set of data from the second gyroscopic sensor when the user performs the first course of action, the received set of data from the second gyroscopic sensor indicating that the user changed an orientation of the user's head;
changing an orientation a view shown on the display screen in accordance with the change of the orientation of the user's head;
receiving vitals data from the at least one vital sensor when the user performs the first course of action;
determining to change a level of difficulty for a second course of action for the user to perform by considering: a) the received vitals data, relative to a level of difficulty of the first course of action, and b) an extent of motion of the lower back region of the user, determined by analyzing the received first set of data from the first gyroscopic sensor, and comparing said analysis of the first set of data with a predetermined threshold motion value; and
displaying on the display screen the second course of action for the user to perform or displaying on the display screen a second set of circumstances that can be interpreted as suggesting to the user to perform the second course of action, the level of difficulty of the second course of action being changed relative to the level of difficulty of the first course of action based on the determining step.

17. The system of claim 16, wherein the second course of action has a higher level of difficulty than the first course of action.

* * * * *